(12) United States Patent
Grey

(10) Patent No.: US 6,403,815 B1
(45) Date of Patent: Jun. 11, 2002

(54) DIRECT EPOXIDATION PROCESS USING A MIXED CATALYST SYSTEM

(75) Inventor: Roger A. Grey, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/997,152

(22) Filed: Nov. 29, 2001

(51) Int. Cl.$^7$ .................. C07Q 301/06; B01J 29/00
(52) U.S. Cl. .............. 549/532; 549/523; 549/524; 502/60; 502/64
(58) Field of Search .................. 549/532, 523, 549/524; 502/60, 64

(56) References Cited

U.S. PATENT DOCUMENTS

| | | | |
|---|---|---|---|
| 3,351,635 A | 11/1967 | Kollar | 260/348.5 |
| 4,367,342 A * | 1/1983 | Wulff et al. | 549/529 |
| 4,410,501 A | 10/1983 | Taramasso et al. | 423/326 |
| 4,833,260 A | 5/1989 | Neri et al. | 549/531 |
| 5,623,090 A | 4/1997 | Haruta et al. | 568/360 |
| 6,008,388 A | 12/1999 | Dessau et al. | 549/531 |
| 6,008,389 A * | 12/1999 | Grosh et al. | 549/533 |
| 6,063,942 A * | 5/2000 | Grey et al. | 549/423 |
| 6,307,073 B1 * | 10/2001 | Jones et al. | 549/532 |

FOREIGN PATENT DOCUMENTS

| | | |
|---|---|---|
| BE | 1001038 A7 | 6/1989 |
| EP | 0978316 A1 | 2/2000 |
| JP | 4-352771 | 12/1992 |
| WO | WO 98/00413 | 6/1997 |

* cited by examiner

Primary Examiner—Floyd D. Higel
Assistant Examiner—Kamal Saeed
(74) Attorney, Agent, or Firm—Kevin M. Carroll

(57) ABSTRACT

The liquid-phase epoxidation reaction of an olefin with hydrogen and oxygen in the presence of a catalyst mixture comprising titanium zeolite and a supported catalyst surprisingly shows higher activity toward epoxide production when the supported palladium catalyst is pre-treated with bromide, or where the reaction is performed in the presence of an alkali or alkaline earth metal bromide compound.

22 Claims, No Drawings

DIRECT EPOXIDATION PROCESS USING A MIXED CATALYST SYSTEM

FIELD OF THE INVENTION

This invention relates to a liquid-phase epoxidation process using a mixed catalyst system to produce epoxides from hydrogen, oxygen, and olefins. The mixed catalyst system contains a titanium zeolite and a supported palladium catalyst. The liquid-phase process is performed in the presence of an alkali or alkaline earth metal bromide compound, or the supported palladium catalyst is pre-treated with bromide prior to use in the process. Surprisingly, the process results in increased activity in olefin epoxidation.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved very useful in epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. For liquid-phase reactions, the catalysts typically contain palladium on a titanium zeolite support. For example, JP 4-352771 discloses the epoxidation of propylene oxide from the reaction of propylene, oxygen, and hydrogen using a catalyst containing a Group VIII to metal such as palladium on a crystalline titanosilicate. The vapor-phase oxidation of olefins has been shown to produce epoxides over gold supported on titanium oxide ($Au/TiO_2$ or $Au/TiO_2$—$SiO_2$), see for example U.S. Pat. No. 5,623,090, and gold supported on titanosilicates, see for example PCT Intl. Appl. WO 98/00413.

Mixed catalyst systems for olefin epoxidation with hydrogen and oxygen have also been disclosed. For example, JP 4-352771 at Example 13 describes the use of a mixture of titanosilicate and Pd/C for propylene epoxidation. U.S. Pat. No. 6,008,388 also describes a catalyst in which palladium is typically added to a titanium zeolite to form a catalyst system, but additionally teaches that the palladium can be incorporated into a support before mixing with the zeolite. In addition, U.S. Pat. No. 6,307,073 discloses a mixed catalyst system that is useful in olefin epoxidation comprising a titanium zeolite and a gold-containing supported catalyst.

One disadvantage of the described direct epoxidation catalysts is that they all show either less than optimal selectivity or productivity. As with any chemical process, it is desirable to develop new direct epoxidation methods and catalysts.

In sum, new processes and catalysts for the direct epoxidation of olefins are needed. I have discovered an effective, convenient epoxidation process that gives good productivity and selectivity to epoxide.

SUMMARY OF THE INVENTION

The invention is an olefin epoxidation process that comprises reacting an olefin, oxygen, and hydrogen in a solvent in the presence of a catalyst mixture. The catalyst mixture comprises a titanium zeolite and a supported palladium catalyst. In one embodiment of the invention, the supported palladium catalyst is pretreated with a bromide-containing agent. In another embodiment of the invention, the reaction is carried out in the presence of an alkali or alkaline earth metal bromide compound. The process is surprisingly found to give higher activity in olefin epoxidation compared to a process that does not include either bromination treatments.

DETAILED DESCRIPTION OF THE INVENTION

The process of the invention employs a catalyst mixture that comprises a titanium zeolite and a supported palladium catalyst. Suitable titanium zeolites are those crystalline materials having a porous molecular sieve structure with titanium atoms substituted in the framework. The choice of titanium zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

Titanium zeolites comprise the class of zeolitic substances wherein titanium atoms are substituted for a portion of the silicon atoms in the lattice framework of a molecular sieve. Such substances are well known in the art.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst mixture employed in the process of the invention also contains a supported palladium catalyst. The supported palladium catalyst comprises palladium and a support. The support is preferably a porous material. Supports are well-known in the art. There are no particular restrictions on the type of supports that are used. For instance, the support can be inorganic oxides, inorganic chlorides, carbon, and organic polymer resins. Preferred inorganic oxides include oxides of Group 2, 3, 4, 5, 6, 13, or 14 elements. Particularly preferred inorganic oxide supports include silica, alumina, titania, zirconia, niobium oxides, tantalum oxides, molybdenum oxides, tungsten oxides, amorphous titania-silica, amorphous zirconia-silica, amorphous niobia-silica, and the like. Preferred organic polymer resins include polystyrene, styrene-divinylbenzene copolymers, crosslinked polyethyleneimines, and polybenzimidizole. Suitable supports also include organic polymer resins grafted onto inorganic oxide supports, such as polyethylenimine-silica. Preferred supports also include carbon. Particularly preferred supports include carbon, silica, silica-aluminas, titania, zirconia, and niobia.

Preferably, the support has a surface area in the range of about 10 to about 700 $m^2/g$, more preferably from about 50 to about 500 $m^2/g$, and most preferably from about 100 to about 400 $m^2/g$. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 0.1 to about 500 $\mu$m, more preferably from about 1 to about 200 $\mu$m, and most preferably from about 10 to about 100 $\mu$m. The average pore diameter is typically in the range of about 10 to about 1000 Å, preferably about 20 to about 500 Å, and most preferably about 50 to about 350 Å.

The catalyst employed in the process of the invention also contains palladium. The typical amount of palladium present in the catalyst will be in the range of from about 0.01 to 20 weight percent, preferably 0.1 to 10 weight percent. The manner in which the palladium is incorporated into the catalyst is not considered to be particularly critical. For example, the palladium (for example, Pd tetraamine bromide) may be supported on the support by impregnation adsorption, ion-exchange, precipitation, or the like.

There are no particular restrictions regarding the choice of palladium compound used as the source of palladium. For example, suitable compounds include the nitrates, sulfates, halides (e.g., chlorides, bromides), carboxylates (e.g. acetate), and amine complexes of palladium.

Similarly, the oxidation state of the palladium is not considered critical. The palladium may be in an oxidation state anywhere from 0 to +4 or any combination of such oxidation states. To achieve the desired oxidation state or combination of oxidation states, the palladium compound may be fully or partially pre-reduced after addition to the catalyst. Satisfactory catalytic performance cam, however, be attained without any pre-reduction.

After catalyst formation, the catalyst may be optionally thermally treated in a gas such as nitrogen, helium, vacuum, hydrogen, oxygen, air, or the like. The thermal treatment temperature is typically from about 50 to about 550° C.

The titanium zeolite and the supported palladium catalyst may be used in the epoxidation process as a mixture of powders or as a mixture of pellets. In addition, the titanium zeolite and supported palladium catalyst may also be pelletized or extruded together prior to use in epoxidation. If pelletized or extruded together, the catalyst mixture may additionally comprise a binder or the like and may be molded, spray dried, shaped or extruded into any desired form prior to use in epoxidation. The weight ratio of titanium zeolite:supported palladium catalyst is not particularly critical. However, a titanium zeolite:supported palladium catalyst ratio of 0.01–100 (grams of titanium zeolite per gram of supported palladium catalyst) is preferred.

In one embodiment of the invention, the supported palladium catalyst of the invention is pre-treated with a bromide-containing agent. The pre-treated palladium catalyst is formed by contacting the palladium catalyst with a bromide-containing agent. The pre-treatment is accomplished in a manner that effectively incorporates bromide onto the supported palladium catalyst. For instance, the supported palladium catalyst can be mixed in the presence of a bromide agent such as HBr. The choice of the bromide agent is not critical, however typical bromide agents include HBr, ammonium bromide, alkylammonium bromides (e.g., tetraalkylammonium bromides), and alkali and alkaline earth metal bromides. Particularly preferred bromide agents include HBr. After bromide pre-treatment, the supported catalyst is typically dried before use in epoxidation reaction.

The amount of bromide agent used in the pre-treatment is not believed to be particularly critical, but at a minimum should be effective to improve catalyst activity as compared to the same process carried out under similar conditions using a non-treated catalyst. Preferably, the amount of bromide agent is sufficient to provide a Br:Pd ratio in the range of 0.01 to about 100, and most preferably in the range of from about 0.1 to about 10.

The process of the invention comprises contacting an olefin, oxygen, and hydrogen in a solvent in the presence of the catalyst mixture. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The process of the invention also requires the use of a solvent. Suitable solvents include any chemical that is a liquid under reaction conditions, including, but not limited to, oxygen-containing hydrocarbons such as alcohols, aromatic and aliphatic solvents such as toluene and hexane, chlorinated aromatic and aliphatic solvents such as methylene chloride and chlorobenzene, and water. Preferred solvents are oxygenated solvents that contain at least one oxygen atom in its chemical structure. Suitable oxygenated solvents include water and oxygen-containing hydrocarbons such as alcohols, ethers, esters, ketones, and the like. Preferred oxygenated solvents include lower aliphatic $C_1$–$C_4$ alcohols such as methanol, ethanol, isopropanol, and tert-butanol, or mixtures thereof, and water. Fluorinated alcohols can be used. A particularly preferred solvent is water. It is also possible to use mixtures of solvents, particularly mixtures of the cited alcohols with water.

Preferably, the process of the invention will also use buffers. If used, the buffer will typically be added to the solvent to form a buffer solution. The buffer solution is employed in the reaction to inhibit the formation of glycols during epoxidation. Buffers are well known in the art.

Suitable buffers include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, acetate, citrate, borate, phthalate, silicate, aluminosilicate, or the like. The cation portion of the salt may include cations such as ammonium, alkylammoniums (e.g., tetraalkylammoniums), alkali metals, alkaline earth metals, or the like. Cation examples include $NH_4$, $NBu^n_4$, Li, Na, K, Cs, Mg, and Ca cations. More preferred buffers include alkali metal phosphate buffers. Buffers may preferably contain a combination of more than one suitable salt. Typically, the concentration of buffer is from about 0.0001 M to about 1 M, preferably from about 0.001 M to about 0.1 M, and most preferably from about 0.005 M to about 0.05 M.

Oxygen and hydrogen are also required for the process of the invention. Although any sources of oxygen and hydrogen are suitable, molecular oxygen and molecular hydrogen are preferred. The molar ratio of hydrogen to oxygen can usually be varied in the range of $H_2:O_2=1:10$ to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to olefin, oxygen and hydrogen, an inert gas carrier may be preferably used in the process. As the carrier gas, any desired inert gas can be used. Suitable inert gas carriers include noble gases such as helium, neon, and argon in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used. The molar ratio of olefin to carrier gas is usually in the range of 100:1 to 1:10 and especially 20:1 to 1:10.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium (or palladium) contained in the titanium zeolite (or palladium supported catalyst) to the olefin that is supplied per unit time. Typically, sufficient catalyst is present to provide a titanium (palladium)/olefin per hour molar feed ratio of from 0.0001 to 0.1.

For the liquid-phase process of the invention, the catalyst mixture is preferably in the form of a suspension or fixed-bed. The process may be performed using a continuous flow, semi-batch or batch mode of operation. It is advantageous to work at a pressure of 1–100 bars. Epoxidation according to the invention is carried out at a temperature effective to achieve the desired olefin epoxidation, preferably at temperatures in the range of 0–250° C., more preferably, 20–200° C.

In another embodiment of the invention, the process is carried out in the presence of an alkali or alkaline earth metal bromide compound. Although any alkali or alkaline earth metal bromide compounds are useful, including NaBr, KBr, CsBr, $MgBr_2$, and $CaBr_2$, cesium bromide is particularly preferred. The alkali or alkaline earth metal bromide compound is simply added to the reaction medium in which the epoxidation is being performed. The alkali or alkaline earth metal bromide compound may be introduced all at once either prior to or following initiation of epoxidation, or it may be added in an incremental or continuous manner.

The amount of the alkali or alkaline earth metal bromide compound is not believed to be particularly critical, but at a minimum should be effective to improve catalyst activity as compared to the same process carried out under similar conditions in the absence of the alkali or alkaline earth metal bromide compound. Preferably, the amount of alkali or alkaline earth metal bromide compound is sufficient to provide a Br:Pd ratio in the range of 0.01 to about 100, and most preferably in the range of from about 0.1 to about 10.

The following examples merely illustrate the invention. Those skilled in the art will recognize many variations that are within the spirit of the invention and scope of the claims.

EXAMPLE 1

Preparation of Stock Solutions

1A: Preparation of Cesium Phosphate Buffer: Cesium hydroxide (22.12 g) is dissolved in deionized water (17.25 g) in a plastic beaker. In a separate container, 85% phosphoric acid (5.85 g) is added with cooling to 400 grams of deionized water. Twenty-five grams of the cesium hydroxide solution is carefully added to the phosphoric acid solution. After the addition, enough deionized water is added to the cesium phosphate buffer to give a volume of 500 mL. The pH of the solution is measured to be 6.9. Two hundred and twenty grams of the above solution (pH=6.9) is then treated with 85% phosphoric acid (1.01 g) to give a cesium phosphate buffer solution with a pH=6.02.

1B: Preparation of HBr Stock Solution: Hydrobromic acid (0.124 g of 48 wt. %) is added to 100 grams of deionized water and mixed well.

EXAMPLE 2

$Pd/Nb_2O_5$ Catalyst Preparation

Catalyst 2A: $Pd/Nb_2O_5$ Preparation

In a glass beaker, $Pd(NH_3)_4(NO_3)_2$ (3.5 g, of an solution containing 10% $Pd(NH_3)_4(NO_3)_2$ is mixed with 16 grams of deionized water. In a separate beaker, niobium oxide powder (12.5 g, from Reference Metals) is slurried in 40 grams of deionized water. The palladium salt solution is added to the niobium oxide slurry with stirring over a 20-minute period. The resulting slurry is stirred at 23° C. for two hours, then the solids are separated by centrifuge. The solids are washed four times by slurrying in 80 grams of water and centrifuging. The solids are then dried in a vacuum oven (1 torr) at 50° C. for 4 hours to give to give 8.6 grams of Catalyst 2A. Elemental analysis shows 0.99 wt. % palladium, 0.18 wt. % nitrogen, and 68 wt. % niobium.

Catalyst 2B: $Pd/Nb_2O_5$ Bromination

Two grams of catalyst 2A ($Pd/Nb_2O_5$) is treated with 10 grams of the HBr stock solution prepared in example 1B. The slurry is stirred at 23° C. for 30 minutes and the solvent is removed by rotoevaporation. The solids are dried in vacuum (0.5 torr) at 50° C. for 4 hours. Elemental analysis shows 0.99 wt % palladium, 0.33 wt % bromide, and 0.26 wt % nitrogen.

EXAMPLE 3

Pd/C Catalyst Preparation

Catalyst 3A: Pd/C Preparation

In a 500-mL roundbottom flask, Acticarbone 2LS activated carbon (16 g, Elf Atochem) is slurried into deionized water (50 g) and methanol (150 mL). Palladium acetate (0.36 g) in acetone (80 mL) is then added to the carbon slurry over a 20-minute period. The resulting slurry is stirred at 50° C. for 1 hour. About half of the solvent is removed by rotoevaporation, then the slurry is filtered and the solids are washed (three times with 100 mL portions of deionized water), air dried, and then dried in a vacuum oven (1 Torr) at 50° C. for 4 hours. Elemental analysis shows 0.93 wt. % palladium.

Catalyst 3B: Pd/C Bromination

A 250-mL roundbottom flask is charged with 8 grams catalyst 3A (Pd/C) and 50 grams of deionized water. Aqueous HBr (30 grams of stock solution from example 1B) is added to the slurry and mixed at 23° C. for 1 hr. The solids are isolated by filtration, washed with 100 mL of deionized water, air dried, and then dried in a vacuum oven (1 torr) at 50° C. for 4 hours. Elemental analysis shows 0.93 wt % palladium and 0.51 wt % bromide.

Catalyst 3C: Pd/C Double Bromination

The bromide-treated Pd/C catalyst 3B (3 g) is slurried in 20 grams of water. Aqueous HBr (15 grams of stock solution as prepared in example 1B) is added to the slurry and mixed at 23° C. for 1 hour. The solids are filtered, washed with 50 mL of deionized water, air dried, and then dried in vacuum (1 torr) at 50° C. for 4 hours. Elemental analysis shows 0.78 wt. % palladium and 1.2 wt. % bromide.

EXAMPLE 4

Pd/Sulfonated Carbon Catalyst Preparation

Catalyst 4A: Preparation of Pd/Sulfonated Carbon

Acticarbone 2LS activated carbon is pretreated and sulfonated according to the procedure reported in European Pat. App. No. 0 978 316 examples 1 and 2. In a 3-neck one-liter flask, concentrated hydrochloric acid (90 g, 37 weight % HCl) is slowly added to deionized water (520 g). Acticarbone 2LS activated carbon (26 g, Elf Atochem) is then added to this solution and the slurry is heated at 80° C. with mixing for 2.5 hours. After cooling to 23° C., the solids are filtered, washed (five times with 100 mL portions of deionized water), and then oven-dried at 120° C. for two hours.

The dried solids are transferred to a 3-neck 250-mL roundbottom flask. Concentrated sulfuric acid (80 mL) is then added over a five-minute period. The thick slurry is heated at 140° C. for 4 hours, cooled, and transferred to a beaker containing 500 grams of deionized water. The solids are isolated by filtration, washed (eight times with 250 mL portions of deionized water), and then air dried.

These solids are transferred to a three-neck 500-mL roundbottom flask and slurried in 140 grams of deionized water. Hydrogen peroxide (24 g, 30 weight percent $H_2O_2$) is then added to the slurry, followed by heating at 70° C. for two hours. After cooling to 23° C., the solids are filtered, washed (with 150 mL of deionized water), and then oven-dried at 120° C. for two hours to give 22 grams of sulfonated carbon. Elemental analysis shows 80 wt. % carbon, 0.5 wt. % sulfur, 0.39 wt. % chloride. 0.2 wt. % silicon, and 0.2 wt. % nitrogen.

In a 250-mL roundbottom flask, sulfonated carbon (6 g, from above) is slurried into deionized water (10 g) and methanol (80 mL). Palladium acetate (0.14 g) in acetone (30 mL) is then added to the carbon slurry over a 5-minute period. The resulting slurry is stirred at 23° C. for 30 minutes, followed by heating at 50° C. for 1 hour. About half of the solvent is removed by rotoevaporation, then the slurry is filtered and the solids are washed (two times with 50 mL portions of deionized water), air dried, and then dried at 110° C. for 2 hours. Elemental analysis shows 0.89 wt. % palladium and 0.6 wt. % sulfur.

Catalyst 4B: Bromination of Pd/sulfonated Carbon

Palladium/sulfonated carbon (1.51 gram) as prepared in example 4A is slurried in 6 grams of the HBr stock solution of example 1B. The mixture is stirred for 30 minutes, the water is removed by rotoevaporation, and the solids are dried in vacuum at 50° C. for 4 hours. Elemental analysis shows 1 wt. % palladium, 0.64 wt. % sulfur, and 0.28 wt. % bromide.

EXAMPLE 5

Pd/Sodium Aluminosilicate Catalyst Preparation

Catalyst 5A: is a commercial 2 wt. % Pd on sodium aluminosilicate available from Sud-Chemie.

Catalyst 5B: Pd/sodium aluminosilicate Bromination

Catalyst 5A (4 g), as obtained from Sud-Chemie, is slurried with 20 grams of the HBr stock solution of Example 1B for 30 minutes at 23° C. The water is removed by rotoevaporation, and the solids are then dried in vacuum at 50° C. for 4 hours. Elemental analysis shows 2.1 wt. % palladium, 4.7 wt. % sodium, 6.9 wt. % aluminum, and 0.29 wt. % bromide.

EXAMPLE 6

Pd/Silica Catalyst Preparation

Catalyst 6: In a 500-mL roundbottom flask, silica (8 g, Davison 952) is slurried into methanol (100 mL). Palladium acetate (0.18 g) in acetone (40 mL) is then added to the flask over a 15-minute period. The resulting slurry is stirred at 50° C. for 1 hour. The solvent is removed by rotoevaporation, the solids are air dried at 110° C. for 2 hours, and then calcined at 450° C. in a 5% oxygen in nitrogen stream flowing at 100 mL/min. Elemental analysis shows 1 wt. % palladium.

EXAMPLE 7

Epoxidation Reactions Using TS-1 and Supported Palladium Catalysts 2A–5B

TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155. The TS-1 is calcined at 550° C. for 4 hours before use.

A 300-cc stainless steel reactor is charged with the supported palladium catalyst (0.2 g), TS-1 (0.5 g, titanium amount=1.6 weight %), deionized water (~120 g), and 13 grams of a cesium phosphate buffer. The reactor is then charged to 200 psig with a feed consisting of 4% hydrogen, 4% oxygen, 5% propylene, 0.5% methane and the balance nitrogen. The pressure in the reactor is maintained at 200 psig via a backpressure regulator with the feed gases passed continuously through the reactor at 1480 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor, containing 1.5 liters of water. The reactor is stirred at 1600 rpm. The reaction mixture is heated to 60° C. (except for runs 3K and 3L which are run at 45° C.) and the gaseous effluent is analyzed by an online GC every hour and the liquid analyzed by offline GC at the end of the 18 hour un.

The results are summarized in Table 1 comparing runs with untreated catalysts 2A, 3A, 4A, and 5A to runs with catalysts 2B, 3B, 3C, 4B, and 5B which are all pre-treated with bromide. The epoxidation results show that the use of supported palladium catalysts that are pre-treated with bromide all give higher activity in olefin epoxidation compared to non-treated catalysts. At the same time, PO/POE selectivity is little changed. "POE" means PO equivalents, which include propylene oxide (PO), propylene glycol (PG), dipropylene glycol (DPG), and acetol.

EXAMPLE 8

Epoxidation Reactions Using TS-1 and Pd/C or Pd/SiO$_2$ in the Presence of CsBr

Run 8A: A 300-cc stainless steel reactor is charged with palladium/carbon catalyst (0.1 g, 3 wt. % Pd, from Englehard), TS-1 (0.5 g, titanium amount=1.6 weight %), deionized water (~120 g), and 13 grams of a cesium phosphate buffer. The epoxidation reaction is then run according to the procedure outlined in Example 7.

Run 8B: The epoxidation reaction is run according to the procedure outlined in Example 8A, except that 1 gram of a cesium bromide solution (prepared by dissolving 0.163 g of cesium bromide in 100 grams of deionized water) is charged to the reactor along with the Pd/C, TS-1, water, and cesium phosphate buffer.

Run 8C: The epoxidation reaction is run according to the procedure outlined in Example 8A, except that catalyst 6 (Pd/SiO$_2$) is used in place of the Pd/C catalyst.

Run 8D: The epoxidation reaction is run according to the procedure outlined in Example 8B, except that catalyst 6 (Pd/SiO$_2$) is used in place of the Pd/C catalyst and only 0.5 g of the cesium bromide solution is used.

The results, summarized in Table 2, show that the use of an alkali metal bromide compound in the epoxidation run results in higher activity with a slight increase in PO/POE selectivity.

TABLE 1

Epoxidation Results for TS-1 + Bromide Treated and Non-treated Pd/support.

| Run # | Catalyst | Bromide Treated | Productivity [1] | PO/POE Selectivity [2] |
|---|---|---|---|---|
| 7A * | 2A | no | 0.13 | 91 |
| 7B | 2B | yes | 0.19 | 90 |
| 7C * | 3A | no | 0.17 | 76 |
| 7D | 3B | yes | 0.23 | 88 |
| 7E | 3C | yes | 0.30 | 84 |
| 7F * | 4A | no | 0.095 | 95 |
| 7G | 4B | yes | 0.17 | 93 |
| 7H * | 5A | no | 0.084 | 93 |
| 7I | 5B | yes | 0.10 | 94 |

[1] Productivity = grams POE produced/gram of catalyst per hour.
[2] PO/POE Selectivity = moles PO/(moles PO + moles propylene glycols) * 100.
* Comparative Example

TABLE 2

Epoxidation Results, With and Without CsBr Addition.

| Run # | Catalyst | Bromine Treated | Productivity [1] | PO/POE Selectivity [2] |
|---|---|---|---|---|
| 8A * | Pd/C | no | 0.068 | 91 |
| 8B | Pd/C | yes | 0.11 | 94 |
| 8C * | Pd/SiO$_2$ | no | 0.052 | 91 |
| 8D | Pd/SiO$_2$ | yes | 0.094 | 91 |

[1] Productivity = grams POE produced/gram of catalyst per hour.
[2] PO/POE Selectivity = moles PO/(moles PO + moles propylene glycols) * 100.
* Comparative Example

I claim:

1. A process for producing an epoxide comprising reacting an olefin, hydrogen and oxygen in a solvent in the presence of a catalyst mixture comprising a titanium zeolite and a supported palladium catalyst comprising palladium and a support, wherein the supported palladium catalyst is pre-treated with bromide-containing agent.

2. The process of claim 1 wherein the titanium zeolite is titanium silicalite.

3. The process of claim 1 wherein the titanium zeolite is TS-1.

4. The process of claim 1 wherein the supported catalyst is comprised of from 0.01 to 10 weight percent palladium.

5. The process of claim 1 wherein the support is carbon, titania, zirconia, niobium oxides, silica, alumina, silica-alumina, tantalum oxides, molybdenum oxides, tungsten oxides, titania-silica, zirconia-silica, niobia-silica, and mixtures thereof.

6. The process of claim 1 wherein the solvent is an oxygenated solvent.

7. The process of claim 6 wherein the oxygenated solvent is selected from the group consisting of alcohols, ethers, esters, ketones, water, and mixtures thereof.

8. The process of claim 1 wherein the olefin is a $C_2$–$C_6$ olefin.

9. The process of claim 8 wherein the olefin is propylene.

10. The process of claim 1 wherein the solvent contains a buffer.

11. The process of claim 1 wherein the bromide-containing agent selected from the group consisting of hydrogen bromide, ammonium bromide, alkylammonium bromides, alkali metal bromides, and alkaline earth metal bromides.

12. A process comprising reacting propylene, hydrogen and oxygen in water in the presence of a catalyst mixture comprising a titanium silicalite and a supported palladium catalyst comprising palladium and a support, wherein the supported palladium catalyst is pretreated with a bromide-containing agent selected from the group consisting of hydrogen bromide, ammonium bromide, alkylammonium bromides, alkali metal bromides, and alkaline earth metal bromides.

13. The process of claim 12 wherein the titanium silicalite is TS-1.

14. The process of claim 12 wherein the support is carbon, titania, zirconia, niobium oxides, silica, alumina, silica-alumina, tantalum oxides, molybdenum oxides, tungsten oxides, titania-silica, zirconia-silica, niobia-silica, and mixtures thereof.

15. The process of claim 12 wherein water contains a buffer comprising an anion and a cation, where the anion is selected from the group consisting of phosphate, carbonate, acetate, citrate, borate, phthallate, silicate, and aluminosilicate and the cation is selected from the group consisting of ammonium, alkylammoniums, alkali metals, and alkaline earth metals.

16. A process for producing an epoxide comprising reacting an olefin, hydrogen and oxygen in a solvent in the presence of a catalyst mixture and an alkali or alkaline earth metal bromide compound, where the catalyst mixture comprises titanium zeolite and a supported palladium catalyst comprising palladium and a support.

17. The process of claim 16 wherein the titanium zeolite is a titanium silicalite.

18. The process of claim 16 wherein the support is carbon, titania, zirconia, niobium oxides, silica, alumina, silica-alumina, tantalum oxides, molybdenum oxides, tungsten oxides, titania-silica, zirconia-silica, niobia-silica, and mixtures thereof.

19. The process of claim 16 wherein the solvent is an oxygenated solvent.

20. The process of claim 19 wherein the oxygenated solvent is selected from the group consisting of alcohols, ethers, esters, ketones, water, and mixtures thereof.

21. The process of claim 16 wherein the alkali or alkaline earth metal bromide compound is cesium bromide.

22. The process of claim 16 wherein the olefin is a $C_2$–$C_6$ olefin.

* * * * *